United States Patent [19]

Hallcher

[11] 4,101,391

[45] Jul. 18, 1978

[54] ELECTROLYTIC OXIDATIVE METHYL-METHYL COUPLING OF CRESOL SALTS

[75] Inventor: Richard C. Hallcher, Bridgeton, Mo.

[73] Assignee: Monsanto Company, St. Louis, Mo.

[21] Appl. No.: 646,725

[22] Filed: Jan. 5, 1976

[51] Int. Cl.$^2$ .................. C25B 3/10; C07C 69/16
[52] U.S. Cl. .................. 204/59 R; 204/73 R; 560/138
[58] Field of Search .................. 204/59 R, 73 R, 72

[56] References Cited

PUBLICATIONS

Suttie, Tetrahedron Letters, No. 12, pp. 953–956, (1969).
Vermillion et al., J. Electrochem. Soc., vol. 111, pp. 1392–1400, 12/66.

*Primary Examiner*—F.C. Edmundson
*Attorney, Agent, or Firm*—Joseph D. Kennedy; John D. Upham

[57] ABSTRACT

Electrolytic oxidation of cresol salts substituted with non-interfering, blocking substituents at least at the 2,4,6-positions relative to the phenolic oxyanion where at least one of the substituents is the cresolic methyl leads to methyl-methyl coupled dehydrodimeric cresols.

20 Claims, No Drawings

ELECTROLYTIC OXIDATIVE METHYL-METHYL COUPLING OF CRESOL SALTS

BACKGROUND OF THE INVENTION

This invention relates to the electrolytic oxidation of appropriately substituted cresol salts to produce the corresponding methyl-methyl coupled dehydrodimeric cresols. More particularly, this invention relates to the electrolytic oxidative methyl-methyl coupling of cresol salts substituted with non-interfering, blocking substituents at least at the 2,4,6-positions relative to the phenolic oxyanion where at least one of the substituents is the cresolic methyl to produce methyl-methyl coupled dehydrodimeric cresol, or simply 1,2-bis(hydroxyaryl)ethanes.

Oxidative methyl-methyl coupling of cresols has previously been accomplished, particularly to prepare the corresponding 1,2-bis(hydroxyaryl)ethanes, by the use of a variety of oxidizing agents. For example, oxidizing agents such as alkaline potassium hexacyanoferrate (III), lead (IV) oxide, silver oxide, air in cumene containing iron (III) stearate, air in chlorobenzene containing 2,2'-azobis(2-methylpropanenitrile)($\alpha,\alpha'$-azobisisobutyronitrile), organic peroxides, and the like have been used for this purpose. Each of these known reagents has certain disadvantages when used in this reaction. These may include low yield, simultaneous production of contaminating by-products such as stilbenequinone structures, and the necessity of using extremely dilute solutions and long reaction periods. Moreover, some of the reagents are relatively expensive.

The disadvantages encountered in the prior art chemical oxidative methyl-methyl coupling processes are overcome by the discovery that appropriately substituted cresol salts undergo electrolytic oxidation to produce methyl-methyl coupled dehydrodimeric cresols (1,2-bis(hydroxyaryl)ethanes).

SUMMARY OF THE INVENTION

According to the present invention, it has been discovered that cresol salts substituted with non-interfering, blocking substituents at least at the 2,4,6-positions relative to the phenolic oxyanion where at least one of the substituents is the cresolic methyl can undergo electrolytic oxidative coupling at the cresolic methyl to yield methyl-methyl coupled dehydrodimeric cresols (1,2-bis(hydroxyaryl)(ethanes).

The methyl-methyl coupled dehydrodimeric cresol products obtained in the present process can be recovered by any of a number of well-known procedures as the free dehydrodimeric cresol or derivatives thereof, such as, for example, the corresponding diacyloxy compounds.

DETAILED DESCRIPTION OF THE INVENTION

Electrolytic oxidation of cresol salts substituted with non-interfering, blocking substituents at least at the 2,4,6-positions relative to the phenolic oxyanion where at least one of the substituents is the cresolic methyl leads to methyl-methyl coupled dehydrodimeric cresols (1,2-bis(hydroxyaryl)ethanes.

The term "non-interfering, blocking substituents" is employed herein to mean substituents which (a) can be present in the cresol salt without causing substantial adverse alteration of either the course of the desired oxidative methyl-methyl coupling of such cresol salts nor the yield of the desired product under process conditions; and (b) are used to block reactive ring positions, such as, for example, the 2,4,6-or ortho-and para-positions relative to the phenolic oxyanion so as to substantially eliminate undesired oxidative ring-to-ring as well as ring-to-oxygen coupled products.

In accordance with the present process, an electric current is passed through a liquid electrolysis medium comprising the cresol salt and solvent. Equations (1) and (2) show the reaction involved, the preparation of 1,2-bis-(3,5-disubstituted-hydroxyaryl)ethanes from a 2,6-disubstituted-4-methylphenoxide and a 2,4-disubstituted-6-methylphenoxide, respectively, being used for purposes of illustration.

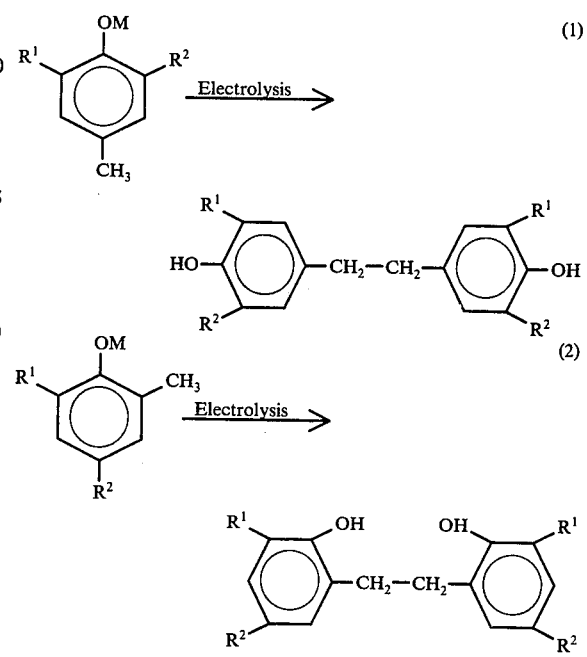

Where the substituents ($R^1$ and $R^2$ as defined hereinbelow) in the 2,6-disubstituted-4-methylphenoxide and 2,4-disubstituted-6-methylphenoxide are alkyls, the products shown in Equations (1) and (2), respectively, will be a 1,2-bis(3,5-dialkyl-4-hydroxyphenyl)ethane and a 1,2-bis(2-hydroxy-3,5-dialkylphenyl)ethane. For example, the product in Equation (1) where $R^1$ and $R^2$ are t-butyls is 1,2-bis(3,5-di-t-butyl-4-hydroxyphenyl)ethane and the product in Equation (2) where $R^1$ and $R^2$ are methyls is 1,2-bis(2-hydroxy-3,5-dimethylphenyl)ethane.

From the above general description it is apparent that the 2,4,6-trimethylphenoxide exhibits a high selectivity toward the ortho methyl-methyl coupled dehydrodimeric cresol product to the substantial exclusion of the corresponding para methyl-methyl coupled product. Indeed, the high selectivity exhibited thereby is quite surprising and unexpected in view of the mixture of dimeric coupled products obtained by means of chemical oxidation of 2,4,6-trimethylphenol as described, for example, in Moore et al, *Journal of the Chemical Society*, 243 (1954).

The cresol salts suitable for use in the present process are represented by the formula:

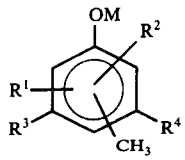

wherein M is either a metal cation having a higher reduction potential (more negative discharge potential) than that of the hydrogen ion (proton), or a quaternary ammonium ion, with suitable metals including, for example, the Group 1a metals (alkali metals) such as lithium, sodium, potassium, rubidium, and cesium, the Group 2a metals (alkaline earth metals) such as magnesium, calcium, strontium, and barium, and the Group 3a metals such as aluminum, gallium, indium, and thallium and suitable quaternary ammonium ions including, for example, tetraalkylammonium such as tetraethylammonium, tetra-n-butylammonium, and the like, alkylarylammonium such as phenyltrimethylammonium, diphenyldimethylammonium, and the like; each of $R^1$ and $R^2$ are independently non-interfering, blocking substituents, including, for example, alkyl of 1 to 10 carbon atoms, alkoxy containing an alkyl of 1 to 10 carbon atoms, amino, alkylamino, and dialkylamino containing alkyls, including cyclic mono-, of 1 to 10 carbon atoms each, or phenyl; and each of $R^3$ and $R^4$ independently are, for example hydrogen or $R^1$ and $R^2$; with the proviso that $R^1$ and $R^2$, and the cresolic methyl are always located at the 2,4,6-positions relative to the phenolic oxyanion. Representative of such cresol salts are the metal and quaternary ammonium salts of 2,4,6-trimethylphenol, 2,4-dimethyl-6-t-butylphenol, 2,4-di-t-butyl-6-methylphenol, 2,6-di-t-butyl-4-methylphenol, 2,4-di-t-pentyl-6-methylphenol, 2,6-di-t-pentyl-4-methylphenol, 2,6-bis(N,N-dimethylamino)-4-methylphenol, 2,4-dimethoxy-6-methylphenol, and the like. Of these, the Group 1a metal and tetraalkylammonium salts of the di-t-butyl-methylphenols and the di-t-pentyl-methylphenols are preferred because (a) they are readily available and/or easily prepared; (b) undesirable side reactions to produce difficult to purify mixtures of coupled products are eliminated by the absence of any benzylic hydrogens in the t-butyl and t-pentyl substituents (although it will be noted that the corresponding 2,4,6-trimethylphenol salt does not present this problem under process condition employed herein); (c) the t-butyl and t-pentyl substituents are easily removed from the methyl-methyl coupled dehydrodimeric product by known procedures to yield 1,2-bis(hydroxyphenyl)ethanes. Of these cresol salts, the most preferred are those of 2,6-di-t-butyl-4-methylphenol.

As is common with salts in general, the cresol salts required for use in the present invention exist as a cation and an anion; that is, as a metal or quaternary ammonium cation and a substituted phenoxide (or cresoxide) anion. Such salts are readily prepared by contacting the corresponding free cresol with an appropriate base of the Group 1a and Group 2a metals, a quaternary ammonium hydroxide, or by heating together the corresponding free cresol and a Group 3a metal. It will be noted, however, that as a consequence of the ready availability and/or ease of preparation of suitable bases of Group 1a metals such as sodium methoxide, potassium t-butoxide, and the like, and tetraalkylammonium hydroxides such as tetraethylammonium hydroxide, tetra-n-butylammonium hydroxide, and the like, coupled with the ease with which such bases react with free cresols to form the corresponding cresol salts when brought into intimate contact with such free cresols, the Group 1a metal and tetraalkylammonium cations are the cations of choice.

It will be noted that the characteristically lower oxidation potential of the phenoxide anion as compared to that of the corresponding free phenol results in a more facile oxidation. This phenomenon permits the electrolytic oxidation of the present process to be carried out even when other easily oxidizable substituents, such as, for example, amino, alkylamino, and dialkylamine are present in the compound. The various undesirable coupling reactions resulting from the oxidation of such easily oxidizable substituents are substantially eliminated in that the facility with which the phenoxide anion is oxidized permits the desired oxidation and subsequent methyl-methyl coupling reaction to be carried out without interference from such substituents.

While not desiring to be bound by the theory of the present invention or to limit the present invention in any way, it will be noted that two different mechanistic pathways are possible for anodic oxidation of phenols: (a) a two-electron loss from the free un-ionized phenol to give a phenoxonium cation and (b) the removal of one electron from the phenoxide anion to give a phenoxy radical. The phenoxonium cation, bearing a positive charge, can readily undergo elimination reactions (when appropriately substituted) and especially addition reactions with any available nucleophile to yield undesirable side products as described in Vermillion, Jr. et al., *Journal of the Electrochemical Society*, 111(12), 1392 (1964). Conversely, the phenoxy radical undergoes coupling reactions, especially carbon-carbon coupling reactions in preference to either elimination or nucleophilic addition reactions. And in the present process, this preference results in the production of the desired methyl-methyl coupled dehydrodimeric cresols.

As indicated hereinabove, the electrolysis of the present invention is effected by passing an electric current through a liquid electrolysis medium comprising the cresol salt and solvent, which medium is in contact with an anode. The medium must have sufficient conductivity to conduct the electrolysis current. While media of poor conductivity can be employed, it is preferred from an economic viewpoint not to have too high a resistance. The required conductivity is generally achieved by employing common supporting electrolytes, such as electrolyte salts whose anions have sufficiently positive discharge potentials, along with a liquid having a fairly good dielectric constant. In general, any combination of electrolyte and solvent can be employed which gives the desired conductivity and is sufficiently compatible with the cresol salt to permit its electrolytic oxidative coupling to the desired product. It is generally desirable to have the electrolyte, when employed, cresol salt, and solvent in a fairly homogeneous dispersion, but a true solution is not required as, for example, many quaternary ammonium salt solutions may, in some respects, be dispersions rather than true solutions. Thus the present invention may use emulsions as well as true solutions so long as sufficient amounts of the cresol salts are dissolved or in solution so as to permit the desired oxidation to occur. Moreover, in emulsions or media having more than one phase, electrolysis can occur in a solution of the components in one of the phases.

The electrolytic oxidative methyl-methyl coupling of the present process can be carried out in either substantially anhydrous media or media containing small amounts of added water. The added water is especially convenient when increased dissolving power of the solvent is desired. Large amounts of added water, however, are to be avoided in that by virtue of the increased nucleophilicity of the solvent, the tendency of the cresol salt, even though present as the phenoxide anion, to undergo a two-electron oxidation to the corresponding phenoxonium cation with its propensity to undergo elimination and nucleophilic addition reactions to give undesirable side-products is significantly increased. When water is added, suitable concentrations will often be in the range of about 0.1 percent to about 20 percent by volume, with the preferred concentration being about 10 percent by volume.

In the solvents employed in the present process, it will generally be desirable to select a solvent (a) which is relatively inert under process conditions and (b) of fairly high dielectric constant in order to lower the electrical resistance. It will be understood, however, that the choice and concentration of electrolyte can also be used to lower electrical resistance.

The term "relatively inert" is employed herein to describe solvents which, under process conditions, (a) do not preferentially undergo electrochemical reaction and (b) do not significantly react with either the starting materials (cresol salts), intermediates generated therefrom, or the desired final products (methyl-methyl coupled dehydrodimeric cresols).

Solvents desirable for use herein have, in addition to characteristics (a) and (b) set forth hereinabove, low nucleophilicity; that is suitable solvents are substantially nonnucleophilic. Further, it is found in practice that it is generally desirable to employ a solvent with a dielectric constant of at least 25, and preferably of at least 50. Examples of such solvents include, for example, acetonitrile, propanenitrile, benzonitrile, dimethylformamide, hexamethylphosphoramide, sulfolane, and the like.

In carrying out the present process, a supporting electrolyte is generally used to enhance conductivity. With some combinations of cresol salts and solvents, an additional electrolyte may not actually be necessary, but in practice a supporting electrolyte is utilized in the present invention. A "supporting electrolyte", as understood by those in the art, is an electrolyte capable of carrying electric current but not discharging under electrolysis conditions. In the present invention this primarily concerns discharge at the anode, as the desired reaction occurs at the anode. Thus the electrolyte employed will generally have anions of more positive anodic discharge potentials than the discharge potential of the cresol salt used. An electrolyte with a similar or slightly lower discharge potential than the cresol salt may be operative to some extent, but yields and current efficiency are adversely affected, so it is generally desirable to avoid any substantial discharge of the electrolyte salt during the electrolysis.

It will be recognized that discharge potentials will vary with anode materials and their surface condition, and various materials in the electrolysis medium. In order for the reaction to proceed, however, it is only necessary to have an effective oxidation of the cresol salt under process conditions. Thus some electrolyte salts may be effective supporting electrolytes under process conditions even though nominally of less positive discharge potential than the cresol salt employed.

In general, any supporting electrolyte salts can be utilized in carrying out the present process, with due consideration to having conditions suitable for discharge of the cresol salt involved. The term "salt" is employed in its generally recognized sense to indicate a compound composed of a cation and an anion, such as produced by a reaction of an acid with a base. The electrolyte salts can be organic, inorganic, or mixtures of such, and composed of simple cations and anions or very large complex cations and anions. In general, however, salts of carboxylic acids are to be avoided in order to eliminate the possibility of Kolbe oxidation.

Certain salts of alkali and alkaline earth metals can be employed as supporting electrolytes to some extent; however, amine and quaternary ammonium salts are generally more suitable and preferred for use in the present invention. Among the quaternary ammonium salts useful are the tetraalkylammonium, for example, tetramethylammonium, tetraethylammonium, tetra-n-propylammonium, and the like, heterocyclic and araalkylammonium salts, for example, benzyltrimethylammonium, and the like.

The term "quaternary ammonium" as employed herein has its usual recognized meaning of a cation having four organic groups substituted on the nitrogen.

Various anions can be used with the foregoing and other cations, such as, for example, perchlorates, tetrafluoroborates, hexafluorophosphates, phosphates, sulfates, sulfonates, tetraphenylborides, and the like. Aromatic sulfonates and similar anions, including those referred to as McKee salts, can be used, as can other hydrotropic salts, although the hydrotropic property may be of no particular significance when employed with solvents having very low water content. Of the foregoing and other anions, the perchlorates are particularly preferred because of their inertness to oxidation and their almost complete lack of complex formation.

The concentration of electrolyte salts, when used, can vary widely, for example, from about 0.5 percent to about 50 percent or more by weight of the electrolysis medium, but suitable concentrations will often be in the range of about 1.0 percent to about 15 percent by weight, or on a molar basis, often in the range of about 0.1 to about 1.0 molar. If, however, it is desired to have all the components in solution, the amount of electrolyte salt utilized will be no greater than will dissolve in the electrolysis medium.

In carrying out the present process, the electrolysis medium (or the anolyte when a divided cell is used) will generally be basic, insofar as acidity and basicity is concerned. It will usually be desirable to operate under basic conditions in order to minimize undesirable side reactions. Attention is drawn to the fact that under basic conditions the phenoxide anion is the predominant species undergoing the desired electrolytic oxidation. And, as noted hereinabove, the characteristically lower oxidation potential of the phenoxide anion results in a more facile oxidation and permits the desired methyl-methyl coupling reaction to be carried out to produce dehydrodimeric cresols (1,2-bis(hydroxyaryl)ethanes). It will be further noted that satisfactory results may also be obtained when the reaction is carried out on the cresol salt in an essentially neutral medium. It will be still further noted that while no particular provisions are necessary to regulate the pH of the electrolysis medium, acidic conditions are to be avoided in that the cresol salts suitable for use herein are converted to the corresponding free, un-ionized cresols under such conditions. These cresols on being subjected to electrolytic oxidation are converted to phenoxonium ions which, as noted hereinabove, undergo undesirable elimination and nucleophilic addition reactions.

In long-term, continuous operations involving re-use of the electrolysis media, it may be desirable to use buffers or to periodically adjust the pH to desired values so as to maintain the desired basic conditions.

The concentration of the cresol salt can vary widely, for example, from about 0.1 percent to about 50 percent or more by weight of the electrolysis medium. In general, however, the concentration will often be in the range between about 1.0 percent and about 15 percent by weight. In continuous operations, the cresol salt concentration will probably be maintained close to some constant value, and the methyl-methyl coupled dehydrodimeric cresol product will also be present in fair amount in the electrolysis medium, depending upon the conversion obtained, as determined by the timing and amount of product separation. For example, the process can be operated at conversion rates of about 20 to 80 percent or so (or other desired rate), and the unreacted cresol salt recycled.

In general the anode potential can be maintained at a selected value or it can be varied. It will be apparent, however, that in order to minimize any possible adverse alteration in the course of the reaction or product distribution, the anode potential is preferably no greater than that which is necessary to effect the desired oxidative methyl-methyl coupling of the cresol salt to the dehydrodimeric cresol. That is, the anode potential will be sufficiently positive to effect a one-electron oxidation of the phenoxide anion of the cresol salt to the phenoxy radical but insufficiently positive to effect a two-electron oxidation to the phenoxonium cation. Suitable anode potentials will often be no more than about $+0.5$ volt (versus a saturated calomel electrode), although it will be recognized that the value will vary with anode materials and their surface conditions, and various materials in the electrolysis medium.

Various current densities can be employed in the present process. It will be desirable to employ high current densities in order to achieve high use of electrolysis cell capacity, and therefore for production purposes it will generally be desirable to use as high a density as feasible, taking into consideration sources and cost of electrical current, resistance of the electrolysis medium, heat dissipation, effect upon yields, and the like. Over broad ranges of current density, the density will not greatly affect the yield. Suitable ranges for efficient operation will generally be in the ranges from a few milliamperes per square decimeter of anode surface, up to 10 or 100 or more milliamperes per square decimeter.

The present electrolysis can be conducted in the various types of electrolysis cells known to the art. In general, such cells comprise a container made of materials capable of resisting action of electrolytes, for example, glass or plastic, and an anode and cathode, which are electrically connected to sources of electric current. The anode can be of any electrode material so long as it is relatively inert under reaction conditions. Anode materials suitable for use in the present process include, for example, graphite, platinum, lead(IV) oxide, gold, and the like. Better results, however, are obtained with anode material of high surface area such as graphite felt.

Any suitable material can be employed as the cathode, various metals, alloys, graphite, and the like being known to the art. For example, platinum, palladium, mercury, lead, and carbon cathodes are suitable, although cathode materials with low hydrogen overpotential, such as, for example, platinum and palladium are preferred.

In the present process either an undivided or a divided cell can be employed. A divided cell contains a suitable barrier material or separator which will prevent the free flow of reactants between the anode and cathode. Generally, the separator is some mechanical barrier which is relatively inert to electrolyte material, for example, a fritted glass filter, glass cloth, asbestos, porous poly(vinyl chloride), and the like. An ion exchange membrane can also be employed.

When a divided cell is used, it will be possible to employ the same electrolysis medium on both the anode and cathode sides, or to employ different media. Ordinarily, it will be desirable to employ the same electrolyte salt and solvent on both the anode and cathode sides; however, in some circumstances, it may be desirable to employ a different catholyte for economy of materials, lower electrical resistance, and the like.

As noted hereinabove, an undivided cell is also suitable for use in the present process. It will be appreciated that this could have advantages for industrial production in that electrical resistance across a cell divider is eliminated.

The electrolysis cells, whether divided or undivided, employed in the procedural Examples hereinbelow are primarily for laboratory demonstration purposes. Production cells are usually designed with a view to the economics of the process, and characteristically have large electrode surfaces, and short distances between electrodes.

For a general description of various laboratory scale cells, see Lund et al, "Practical Problems in Electrolysis," in *Organic Electrochemistry* (Baizer, ed.), Marcel Dekker, New York, 1973, pp. 165–249, and for some considerations of industrial cell designs, see Danly, "Industrial Electroorganic Chemistry," in Ibid, pp. 907–946.

The present process is suited to either batch or continuous operations. Continuous operations can involve recirculation of a flowing electrolyte stream, or streams between the electrodes, with continuous or intermittent sampling of the stream for product removal.

Similarly, additional reactants can be added continuously or intermittently, and electrolyte salt or other electrolyte components can be augmented, replenished, or removed as appropriate.

The electrolysis can be conducted at ambient temperatures, or at higher or lower temperatures. However, it may be desirable to avoid excessively high or elevated temperatures in that increased production of undesirable side products may result. It may also be desirable to avoid elevated temperatures if volatile materials (solvents) are utilized so that such materials will not escape, and various cooling means can be used for this purpose. Cooling to ambient temperatures is sufficient, but, if desired, temperatures down to 0° C or lower can be employed so long as the temperature is sufficient to permit the desired oxidation and subsequent methyl-methyl coupling to occur. The amount of cooling capacity needed for the desired degree of control will depend upon the cell resistance and the electrical current drawn. If desired, cooling can be effected by immersing the electrolysis cell in an ice or ice-salt bath or by permitting a component, such as the solvent, to reflux through a cooling condenser. Pressure can be employed to permit electrolysis at higher temperatures with volatile solvents, but unnecessary employment of pressure is usually undesirable from an economic standpoint.

The present electrolysis is preferably carried out under an inert atmosphere or the like in order to remove and prevent the presence of residual oxygen (and moisture when anhydrous conditions are desired). Nitrogen gas admirably serves this purpose. It is passed through the electrolysis medium both prior to and during the electrolysis in order to minimize undesirable side reactions, such as, for example, peroxide formation.

The dehydrodimeric cresol products (1,2-bis(hyroxyarylethanes) is obtained in the present process can be readily recovered by any of a number of well known procedures as the free dehydrodimeric cresol or derivatives thereof, such as, for example, the corresponding diacyloxy compound. It will be understood, however, that the isolation procedures employed in the procedural Examples and discussed hereinbelow are primarily for illustrative purposes. Other procedures can be employed, and may be preferred, for commercial use.

Upon completion of the electrolysis, the reaction mixture is made acidic by the addition of an appropriate mineral acid, such as, for example, concentrated hydrochloric acid and filtered. The anode, if graphite felt, may be either washed intact with an appropriate solvent, or it may initially be chopped into a finely divided mass prior to being washed to extract the dehydrodimeric cresol product. Suitable solvents include, for example, chloroform, methylene chloride, and the like.

The reaction mixture filtrate and the extraction solvent washings are combined and evaporated in vacuo to yield a solid residue which is subsequently dissolved in an appropriate solvent, such as, for example, chloroform or methylene chloride, washed with water, dried over an appropriate dessicant, such as, for example, magnesium sulfate, filtered, and evaporated in vacuo to yield the crude dehydrodimeric cresol product. Recrystallization from a suitable solvent such as ethanol, acetone, and the like yields the pure dehydrodimeric cresol product.

Small amounts of numerous side products are also produced during the present process as indicated by vapor phase chromatographic analysis of the filtrate. For example, the side products produced from the electrolytic oxidative methylmethyl coupling of sodium 2,6-di-t-butyl-4-metyl-phenoxide include 2,6-di-t-butyl-4-methylphenol, 2,6-di-t-butyl-4-methoxy-methylphenol, and 3,5,3',5'-tetra-t-butyl-4,4'-stilbenequinone.

Instead of being isolated as the free dehydrodimeric cresol, the product is alternatively isolated as the corresponding diacyloxy compound. The crude dehydrodimeric cresol, isolated as described hereinabove, is dissolved in an appropriate solvent, such as, for example, chloroform or absolute ether and treated at low temperatures, such as, for example about 0° C under an inert atmosphere with an acylating agent such as acetyl chloride, acetic anhydride, and the like in the presence of a suitable base, such as, for example, triethylamine. The resulting solution is washed successively with water, a saturated aqueous solution of a mild base, such as, for example, sodium bicarbonate, and water, dried over an appropriate dessicant, and evaporated in vacuo. Vacuum distillation of the low-boiling fraction from the oily residue gives the diacyloxy compound which is readily recrystallized from a suitable solvent such as ethanol, acetone, and the like to yield the pure product.

It will be noted that since the diacyloxy derivatives are esters, the free dehydrodimeric cresols can, if desired, be readily recovered therefrom by standard procedures.

It will also be noted that when, in addition to the phenolic hydroxyl groups, other easily acylated substituents, such as, for example, primary or secondary amino groups are present in the molecule they too will undergo acylation. And unless the polyacylated compound is desired, it may be preferable in such instances to isolate the product as the free dehydrodimeric cresol.

When at least $R^1$ and $R^2$ are tertiary alkyl groups, such as, for example, t-butyl or t-pentyl, the dehydrodimeric cresol product can be easily dealkylated by known procedures. For example, 1,2-bis(3,5-di-t-butyl-4-hydroxyphenyl)ethane, upon being heated with a catalytic amount of p-toluenesulfonic acid, is readily debutylated to give 1,2-bis(4-hydroxyphenyl)ethane, also known as bisphenol E. It will be noted that the isobutene generated during the debutylation reaction can be reacted with p-cresol (4-methylphenol) to give 2,6-di-t-butyl-4-methylphenol.

Thus the present invention provides a convenient route from appropriately substituted cresol salts to bisphenol E.

The following examples illustrate the present invention and the manner by which it can be practiced.

EXAMPLE 1

1,2-Bis(3,5-di-t-butyl-4-hydroxyphenyl)ethane

Procedure A– 2,6-Di-t-butyl-4-methylphenol (13.2 grams, 0.06 mole) was dissolved in 75 milliliters of absolute methanol. Nitrogen gas was passed through the solution while sodium methoxide (3.24 grams, 0.06 mole) was added at ambient temperature. The reaction mixture was warmed to about 50° C an maintained there for about 15 minutes. Thereafter the methanol was evaporated to dryness to yield the desired sodium 2,6-di-t-butyl-4-methyl-phenoxide.

A 400-milliliter beaker lined with a graphite felt anode (4 inches × 7 inches; 10.16 centimeters × 17.78 centimeters) and with a platinum cathode (1 inch × 2 inches; 2.54 centimeters × 5.08 centimeters) placed in the center was used as an electrolysis cell. A saturated calomel electrode was placed just next to the anode surface to serve as a reference electrode.

The electrolysis cell was charged with 300 milliliters of acetonitrile, 6.9 grams (0.03 mole) of tetraethylammonium perchlorate, and the previously prepared salt of the phenol. Nitrogen gas was continuously passed through the solution during the electrolysis which was conducted at ambient temperatures at an anode potential of +0.3 volt versus the saturated calomel electrode. The initial current of 210 milliamperes decreased to 13 milliamperes over a 16-hour period. Upon completion of the electrolysis, the reaction mixture was acidified with 15 milliliters of concentrated hydrochloric acid an filtered. The felt anode was chopped into a finely divided mass and washed with three 75-milliliter portions of chloroform, which were combined with the filtrate. Evaporation of the solvent in vacuo yielded a solid residue which was dissolved in 100 milliliters of chloroform, washed with water, dried over anhydrous magnesium sulfate, filtered, and evaporated. The orange residue was dissolved in hot ethanol, seeded with crystals of 1,2-bis(3,5-di-t-butyl-4-hydroxyphenyl)ethane, and allowed to stand in the cold. The crystals were collected by suction filtration and dried to yield 10.4 grams 79.1 percent) of 1,2-bis(3,5-t-butyl-4-hydroxyphenyl)ethane, melting point 169°–170° C.

Vapor phase chromatographic analysis of the filtrate showed the presence of small amounts of numerous side-products, including 2,6-di-t-butyl-4-methylphenol, 2,6-di-t-butyl-4-methoxymethylphenol, and 3,5,3′,5′-tetra-t-butyl-4,4′-stil-benequinone.

Procedure B– A two-compartment H-type electrolysis cell in which a 400-milliliter capacity anode compartment and a 50-milliliter capacity cathode compartment were separated by a 1-inch (2.54 centimeter) diameter glass frit was employed. The anode compartment was lined with a graphite felt anode (4 inches × 7 inches; 10.16 centimeters × 17.78 centimeters) with a saturated calomel electrode positioned just next to its surface to serve as a reference electrode, and the cathode compartment contained a platinum cathode (1 inch × 2 inches; 2.54 centimeters × 5.08 centimeters).

The sodium salt of the phenol was prepared from 4.4 grams (0.02 mole) of 2.6-di-t-butyl;-4-methylphenol, 3.24 grams (0.06 mole) of sodium methoxide, and 75 milliliters of absolute methanol as described in Procedure A above.

The anode compartment was charged with 200 milliliters of solution made up from the previously prepared sodium salt of the phenol and 4.6 grams (0.02 mole) of tetraethylammonium perchlorate dissolved in 10 percent aqueous acetonitrile. The cathode compartment was charged with 50 milliliters of the same solution but without the sodium salt of the phenol. Electrolysis under a nitrogen atmosphere at ambient temperatures proceeded for 8.5 hours at +0.3 volt versus the saturated calomel electrode. The initial current of 150 milliamperes decreased to 30 milliamperes over the electrolysis period. The anode compartment electrolysis mixture was acidified. with 5 milliliters of concentrated hydrochloric acid and the product isolated as described in Procedure A above to yield 3.8 grams of solid residue. Recrystallization twice from acetone yielded 2.1 grams (47.9 percent) of 1,2-bis(3,5-di-t-butyl-4-hydroxyphenyl)ethane as white crystals, melting point 171°–172° C.

EXAMPLE 2

1,2-Bis(2-acetoxy-3,5-dimethylphenyl)ethane

Procedure A— Sodium 2,4,6-trimethylphenoxide was prepared from a solution of 2.72 grams(0.02 mole) of 2,4,6-trimethylphenol dissolved in 60 milliliters of absolute methanol and 1.08 grams (0.02 mole) of sodium methoxide as described in Procedure A of EXAMPLE 1 above. The methanol was evaporated in vacuo and the residue dissolved in 300 milliliters of acetonitrile containing 6.9 grams (0.03 mole) of tetracethylammonium perchlorate, the entire solution being charged to the electrolysis apparatus described in Procedure A of EXAMPLE 1 above. Electrolysis was conducted at ambient temperatures under a nitrogen atmosphere over an 8.5-hour period at +0.3 volt versus the saturated calomel electrode. The initial current of 150 milliamperes decreased to 20 milliamperes over the electrolysis period. The reaction mixture was acidified with 5 milliliters of concentrated hydrochloric acid and filtered. The felt anode was washed successively with two 50-milliliter portions each of acetonitrile and chloroform which were combined with the reaction mixture filtrate. Evaporation of the solvent in vacuo yielded a solid residue which was dissolved in chloroform and cooled to 0° C while 3.92 grams (0.043 mole) of triethylamine were added under a nitrogen atmosphere. Acetyl chloride (3.02 grams, 0.038 mole) was added dropwise over a 1-hour period. Upon completion of the addition, the reaction mixture was allowed to warm to ambient temperature over a 1-hour period. The chloroform solution was washed successively with 100-milliliter portions of water, saturated aqueous sodium bicarbonate solution, and water, dried, and evaporated. Following removal of the low-boiling fraction (mostly 2,4,6-trimethylphenyl acetate) of the oily residue by vacuum distillation at 0.3 millimeter of mercury, there remained a solid residue which was recrystallized from ethanol to yield 2.84 grams (80.2 percent of 1,2-bis(2-acetoxy-3,5-dimethylphenyl)ethane, melting point 130°–131° C.

Procedure B — A solution of 5.44 grams (0.04 mole) of 2,4,6-trimethylphenol dissolved in 300 milliliters of acetonitrile containing 10.2 grams (0.03 mole) of tetra-n-butylammonium perchlorate and 5 milliliters of 37 percent (by weight) aqueous tetra-n-butylammonium hyroxide was charged to the electrolysis apparatus described in Procedure A of EXAMPLE 1. Electrolysis was conducted at ambient temperatures under a nitrogen atmosphere over a 16-hour period at +0.4 volt versus the saturated calomel electrode. A constant current of 200 milliamperes was maintained throughout the electrolysis period. A solid residue was obtained as described in Procedure A of EXAMPLE 2 above. It was dissolved in ether, washed with water, dried over anhydrous magnesium sulfate, and evaporated in vacuo. The residue was dissolved in absolute ether and treated with 8.0 grams (0.079 mole) of triethylamine and 10.0 grams (0.13 mole) of acetyl chloride as described in Procedure A of EXAMPLE 2 above to yield the crude product. Recrystallization from ethanol and concentration of the resulting mother liquor following the initial collection of crystals yielded 5.7 grams (80.5 percent) of 1,2-bis(2-acetoxy-3,5-dimethylphenyl)ethane, melting point 130°–131° C.

EXAMPLE 3

1,2-Bis(4-hydroxyphenyl)ethane (Bisphenol E)

A solution of 5.0 grams (0.011 mole) of 1,2-bis(3,5-di-t-butyl-4-hydroxyphenyl)ethane dissolved in 30 milliliters of tetralin containing 0.2 gram (0.0012 mole) of p-toluensulfonic acid was heated to reflux for a total of 3 hours. The reaction mixture was cooled and poured into 50 milliliters of water. The precipitated solid was collected by suction filtration and recrystallized from ethanol to yield 2.3 grams (97 percent) of bisphenol E, melting point 199°–200° C.

The 1,2-bis(hydroxyaryl)ethane, as dehydrodimeric cresols, are useful as bactericides, chemical intermediates, copolymers, and antioxidants. They are used to stabilize such materials as animal and vegetable fats or oils, gasoline, lubricants, polyalkenes such as polyethylene and polypropylene, and both natural and synthetic rubber. The dehydrodimeric cresols in which the phenolic hydroxyl group is not sterically hindered by large bulky substituents in the ortho positions relative to the phenolic hydroxyl may also be used in the preparation of resins, for example, polyesters, polycarbonates, and the like resins, wherein they are used as the dehydroxy compound which is reacted either with phesgene, dibasic acids, dibasic acid halides polyepoxides, polyurethanes, and the like.

While the invention has been described with respect to various specific examples and embodiments thereof, it will be understood that the invention is not limited thereto and that many alternatives, modifications, and variations will be apparent to those skilled in the art in light of the foregoing description. Accordingly, it is intended to embrace all such alternatives modifications, and variations as fall within the spirit and broad scope of the invention.

What is claimed is:

1. The process of electrolytic oxidative methyl-methyl coupling of cresol salts substituted with non-interfering, blocking substituents at least at the 2,4,6-positions relative to the phenolic oxyanion where at least one of the substituents is the cresolic methyl, which process comprises electrolytic oxidation at the anode by electrolysis at no more than about 0.5 volts (versus the saturated calomel electrode) in a liquid electrolysis medium comprising such cresol salt and a substantially non-nucleophilic solvent, and thereafter recovering a methyl-methyl coupled dehydrodimeric cresol.

2. The process of claim 1 wherein the cresol salt is a 2,4,6-trialkylphenol salt.

3. The process of claim 2 wherein the 2,4,6-trialkylphenol salt is a 2,6-di-t-butyl-4-methylphenol salt.

4. The process of claim 2 wherein the 2,4,6-trialkylphenol salt is a 2,4,6-trimethylphenol salt.

5. The process of claim 1 wherein the cresol salt is a Group 1a metal or tetraalkylammonium 2,4,6-trialkylphenoxide and the methyl-methyl coupled dehydrodimeric cresol is a 1,2-bis(3,5-dialkyl-hydroxyphenyl)ethane.

6. The process of claim 5 wherein the Groups 1a or tetraalkylammonium 2,4,6-trialkylphenoxide is sodium 2,6-di-t-butyl-4-methylphenoxide and the 1,2-bis(3,5-dialkylhydroxyphenyl)ethane is 1,2-bis(3,5-di-t-butyl-4-hydroxyphenyl)ethane.

7. The process of claim 5 wherein the Group 1a or tetraalkylammonium 2,4,6-trialkylphenoxide is sodium 2,4,6-trimethylphenoxide and the 1,2-bis(3,5-dialkyl-hydroxyphenyl)ethane is 1,2-bis (2-hydroxy-3,5-dimethylphenyl)ethane.

8. The process of claim 5 wherein the Group 1a or tetraalkylammonium 2,4,6-trialkylphenoxide is tetra-n-butylammonium 2,4,6-trimethylphenoxide and the 1,2-bis(3,5-dialkylhydroxyphenyl)ethane is 1,2-bis(2-hydroxy-3,5-dimethylphenyl)-ethane.

9. The process of claim 1 wherein the electrolysis medium is basic.

10. The process of claim 1 wherein the solvent is substantially anhydrous.

11. The process of claim 10 wherein the substantially anhydrous solvent is acetonitrile.

12. The process of claim 1 wherein the solvent contains small amounts of added water.

13. The process of claim 12 wherein the solvent containing small amounts of added water is acetonitrile.

14. The process of claim 12 wherein the concentration of the small amounts of added water is about 10 percent by volume.

15. The process of claim 1 wherein a supporting electrolyte is used.

16. The process of claim 15 wherein the concentration of the supporting electrolyte is between about 1.0 percent and about 15 percent by weight.

17. The process of claim 15 wherein the supporting electrolyte is a quaternary ammonium salt.

18. The process of claim 17 wherein the quaternary ammonium salt is tetraethylammonium perchlorate.

19. The process of claim 1 wherein a graphite felt anode and a platinum cathode are used.

20. The process of claim 1 wherein the concentration of the cresol salt in the electrolysis medium is between about 1.0 percent and about 15 percent by weight; the anode potential is sufficient to effect oxidative methyl-methyl coupling of the cresol salt; and the electrolysis is conducted at ambient temperatures.

* * * * *